United States Patent
Heaton et al.

(10) Patent No.: US 9,549,856 B2
(45) Date of Patent: Jan. 24, 2017

(54) MODULAR, REDUCED-PRESSURE, WOUND-CLOSURE SYSTEMS AND METHODS

(75) Inventors: Keith Patrick Heaton, Poole (GB); Christopher Guy Coward, Wareham (GB); Colin John Hall, Poole (GB)

(73) Assignee: KCI Licensing, Inc., San Antonio, TX (US)

( * ) Notice: Subject to any disclaimer, the term of this patent is extended or adjusted under 35 U.S.C. 154(b) by 1218 days.

(21) Appl. No.: 13/467,176

(22) Filed: May 9, 2012

(65) Prior Publication Data

US 2012/0220985 A1 Aug. 30, 2012

Related U.S. Application Data (62) Division of application No. 12/467,168, filed on May 15, 2009, now Pat. No. 8,197,467.

(Continued)

(51) Int. Cl.
*A61M 1/00* (2006.01)
*A61F 13/00* (2006.01)
*A61B 17/00* (2006.01)

(52) U.S. Cl.
CPC ..... *A61F 13/00068* (2013.01); *A61B 17/0057* (2013.01); *A61F 13/00025* (2013.01);
(Continued)

(58) Field of Classification Search
CPC .. A61M 27/00; A61M 1/0088; A61M 1/0092; A61M 1/0058; A61M 1/0023; A61F 13/00068; A61F 13/00025; A61F 13/00989; A61F 13/00034; A61F 13/00038; A61F 13/00029; A61F 13/987; A61B 2017/00676; A61B 2017/00646; A61B 2017/00575; A61B 17/0057; Y10T 156/1304; Y10T 156/1056; Y10T 156/1062; Y10T 156/1057; Y10T 156/1052; Y10T 29/49; Y10T 29/49826; Y10S 128/26

See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 A1 8/1982
AU 745271 4/1999
(Continued)

OTHER PUBLICATIONS

N.A. Bagautdinov, "Variant of External Vacuum Aspiration in the Treatment of Purulent Diseases of the Soft Tissues," Current Problems in Modem Clinical Surgery: Interdepartmental Collection, edited by V. Ye Volkov et al. (Chuvashia State University, Cheboksary, U.S.S.R. 1986);pp. 94-96 (copy and certified translation).

(Continued)

*Primary Examiner* — Tatyana Zalukaeva
*Assistant Examiner* — Ariana Zimbouski (57) ABSTRACT

A modular, reduced-pressure, wound-closure system for providing a closing force on a surface would includes a flexible strap operable to be formed into a closed loop inbound and around the surface wound and a plurality of modular closing members coupled to the flexible strap. A reduced-pressure source is fluidly coupled to the plurality of modular closing members. The modular closing members are operable to generate a closing force on the surface wound. A portion of the modular closing members are releasably attached to the patient's epidermis proximate the surface wound and another portion are attached to the (Continued)

flexible strap. A reduced pressure from the reduced-pressure source is delivered to each modular closing member to generate the closing force on the surface wound. Methods and other systems are presented.

12 Claims, 5 Drawing Sheets

Related U.S. Application Data (60) Provisional application No. 61/109,410, filed on Oct. 29, 2008, provisional application No. 61/109,486, filed on Oct. 29, 2008, provisional application No. 61/109,390, filed on Oct. 29, 2008, provisional application No. 61/109,448, filed on Oct. 29, 2008.

(52) U.S. Cl.
CPC .. *A61F 13/00034* (2013.01); *A61F 13/00987* (2013.01); *A61M 1/0088* (2013.01); *A61B 2017/00575* (2013.01); *A61B 2017/00646* (2013.01); *A61B 2017/00676* (2013.01); *A61F 13/00029* (2013.01); *A61F 13/00038* (2013.01); *A61M 1/0092* (2014.02); *Y10T 29/49* (2015.01); *Y10T 29/49826* (2015.01); *Y10T 156/1052* (2015.01); *Y10T 156/1056* (2015.01); *Y10T 156/1057* (2015.01); *Y10T 156/1062* (2015.01); *Y10T 156/1304* (2015.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,128,735 B2 | 10/2006 | Weston |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2005/0085795 A1 | 4/2005 | Lockwood |
| 2006/0079852 A1 | 4/2006 | Bubb |
| 2007/0282309 A1* | 12/2007 | Bengtson .............. A61M 27/00 604/541 |

FOREIGN PATENT DOCUMENTS

| | | |
|---|---|---|
| AU | 455496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |

(56) References Cited

FOREIGN PATENT DOCUMENTS

| GB | 692578 | 6/1953 |
|---|---|---|
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |
| WO | WO01/85248 A | 11/2001 |
| WO | WO2007041642 A | 4/2007 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov, Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax, " Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

(56) References Cited

OTHER PUBLICATIONS

V.A.C. ® Therapy Clinical Guidelines: A Reference Source for Clinicians (Jul. 2007).
International Search Report for Application No. PCT/US2009/044245 mailed Nov. 5, 2009.

* cited by examiner

MODULAR, REDUCED-PRESSURE, WOUND-CLOSURE SYSTEMS AND METHODS

RELATED APPLICATIONS

The present application is a divisional of U.S. patent application Ser. No. 12/467,168, filed May 15, 2009 now U.S. Pat. No. 8,197,467 entitled "Modular, Reduced-Pressure, Wound-Closure Systems and Methods", which claims the benefit, under 35 USC §119(e), of the filing of U.S. Provisional Patent Application Ser. No. 61/109,410, entitled "Reduced-Pressure, Wound-Closure System and Method," filed Oct. 29, 2008; U.S. Provisional Patent Application Ser. No. 61/109,486, entitled "Reduced-Pressure, Abdominal Treatment System and Method," filed Oct. 29, 2008; U.S. Provisional Patent Application Ser. No. 61/109,390, entitled "Open-Cavity, Reduced-Pressure Wound Dressing and System," filed Oct. 29, 2008; and U.S. Provisional Patent Application Ser. No. 61/109,448, entitled "Reduced-Pressure, Deep-Tissue Closure System and Method," filed Oct. 29, 2008. All of these provisional applications are incorporated herein by reference for all purposes.

BACKGROUND

The present invention relates generally to medical treatment systems and, more particularly, to modular, reduced-pressure, wound-closure systems and methods.

Whether the etiology of a wound, or damaged area of tissue, is trauma, surgery, or another cause, proper care of the wound is important to the outcome. Unique challenges exist when the wound involves locations that require reentry, such as the peritoneal cavity and more generally the abdominal cavity. Many times when surgery or trauma involves the abdominal cavity, establishing a wound management system that facilitates reentry allows for better and easier care and helps to address such things as peritonitis, abdominal compartment syndrome (ACS), and infections that might inhibit final healing of the wound and the internal organs. In providing such care, it may be desirable to remove unwanted fluids from the cavity, help approximate the fascia and other tissues, or finally to help provide a closing force on the wound itself at the level of the epidermis. Unless otherwise indicated, as used herein, "or" does not require mutual exclusivity.

Currently, an abdominal opening on the epidermis may be closed using sutures, staples, clips, and other mechanical devices to allow the skin to be held and pulled. Such devices often cause puncture wounds or other wounds. Moreover, if severe edema occurs, tremendous pressure may be placed on the closure device and the pressure may cause harm. For example, if the pressure rises due to edema, the sutures may tear out.

With respect to an overall system for allowing reentry into the abdominal cavity, a number of techniques have been developed. One approach is to place towels into the cavity and then use clips, such as hemostats, to close the skin over the towels. While simple and fast, the results are regarded as suboptimal. Another approach is the so-called "Bogota bag." With this approach, a bag is sutured into place to cover the open abdomen in order to provide a barrier. Still another approach, sometimes called a "vac pack," is to pack towels in the wound and then place a drain into the abdomen and cover the abdomen with a drape. Finally, a reduced pressure approach has been used. Such an approach is shown in U.S. Pat. No. 7,381,859 to Hunt et al. and assigned to KCI Licensing, Inc. of San Antonio, Tex. U.S. Pat. No. 7,381,859 is incorporated herein by reference for all purposes.

SUMMARY

Problems with existing wound closure devices and reduced-pressure treatment systems are addressed by the systems, apparatus, and methods of the illustrative embodiments described herein. According to one illustrative embodiment, a modular, reduced-pressure wound-closure system includes a flexible strap operable to be formed into a closed loop and a plurality of modular closing members selectively coupled to the flexible strap. Each of the plurality of modular closing members includes an attachment member, a sealed contracting member, and a connection member. Each attachment member is for releasably attaching to a portion of the patient's epidermis proximate an edge of a surface wound and to a portion of a sealed contracting member. Each sealed contracting member is operable to contract under reduced pressure. Each connection member is coupled to a corresponding sealed contracting member and is operable to selectively couple to the flexible strap. Each modular closing member also includes a reduced-pressure interface fluidly coupled the sealed contracting member for delivering a reduced pressure to the sealed contracting member. The modular, reduced-pressure wound-closure system also includes a reduced-pressure source fluidly coupled to each reduced-pressure interface of each of the plurality of modular closing members.

According to another illustrative embodiment, a method of manufacturing a modular, reduced-pressure, wound-closure system includes the steps of forming a flexible strap operable to be shaped into a closed loop and forming a plurality of modular closing members. The step of forming a plurality of modular closing members may include, for each of the plurality of modular closing members, the steps of forming an attachment member for releasably attaching to a portion of the patient's epidermis proximate an edge of the wound and forming a sealed contracting member. The sealed contracting member is operable to contract when placed under reduced pressure. The step of forming a plurality of modular closing members further includes coupling a second end of the sealed contracting member to the attachment member and forming a connection member. The connection member is operable to selectively couple to the flexible strap. The step of forming a plurality of modular closing members further includes coupling the connection member to a first end of the sealed contracting member. The illustrative method may further include the steps of fluidly coupling the closing, reduced pressure source to the plurality of modular closing members. The closing reduced-pressure source is operable to deliver a reduced pressure to each of the plurality of modular closing members.

According to another illustrative embodiment, a method of providing a closing force to a surface wound on a patient includes the steps of providing a flexible strap operable to be shaped into a closed loop and providing a plurality of modular closing members. The method of providing a closing force further includes the steps of shaping the flexible strap into a closed loop proximate the surface wound and providing a reduced pressure source. The method of providing a closing force further includes the steps of fluidly coupling the reduced-pressure source to the plurality of modular closing members and delivering reduced pressure to each of the plurality of modular closing members. When reduced pressure is delivered, the modular closing members generate a closing force. In this illustrative embodiment, each of the plurality of modular closing members includes an attachment member for releasably attaching to a portion of the patient's epidermis proximate an edge of the surface wound and a sealed contracting member, which has a first end and a second end. The second end of the sealed contracting member is coupled to the attachment member. The sealed contracting member is operable to contract when placed under reduced pressure. Each of the plurality of modular closing members further includes a connection member coupled to the first end of the sealed contracting member and a reduced-pressure interface fluidly coupled the sealed contracting member for delivering reduced pressure to the sealed contracting member.

Other objects, features, and advantages of the illustrative embodiments will become apparent with reference to the drawings and detailed description that follow.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
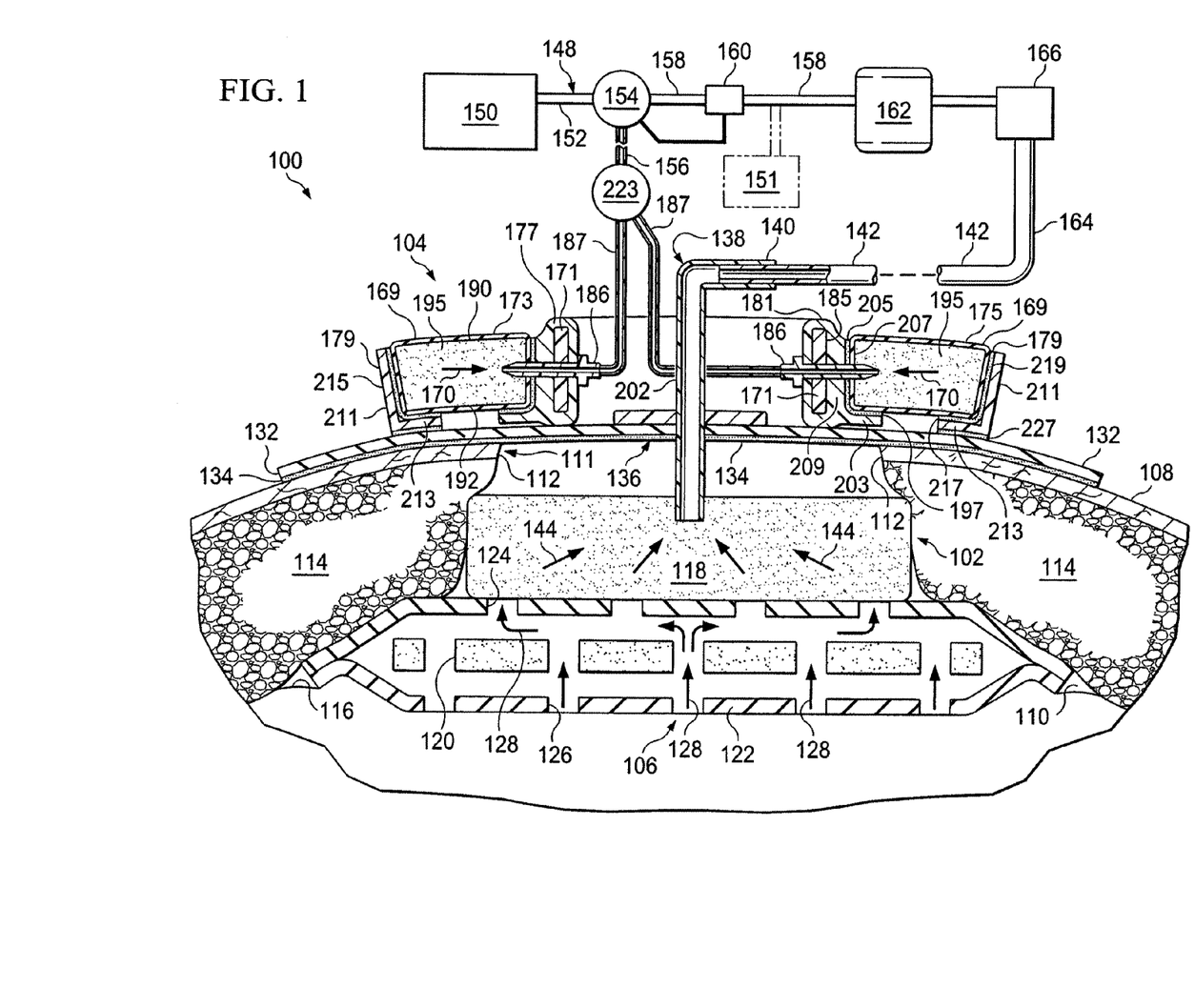
FIG. 1 is a schematic cross-section, with a portion presented as a block diagram, of an illustrative embodiment of a modular, reduced-pressure, wound-closure and treatment system.

Referring to FIG. 1, an illustrative embodiment of a reduced-pressure, wound-closure and treatment system 100 is presented. The reduced-pressure, wound-closure and treatment system 100 may include a reduced-pressure treatment subsystem 102 and a modular, reduced-pressure, wound-closure subsystem 104. The reduced-pressure treatment subsystem 102 may be used for treating a tissue site 106 with a reduced pressure. The tissue site 106 may be the bodily tissue of any human, animal, or other organism, including bone tissue, adipose tissue, muscle tissue, dermal tissue, vascular tissue, connective tissue, cartilage, tendons, ligaments, or any other tissue. The tissue site 106 may be within a body cavity, such as an abdominal cavity 110, and may include various tissue layers including a wound in epidermis 108. Treatment with the reduced-pressure treatment subsystem 102 may include removing fluids, such as ascites or exudates, delivering reduced pressure, or providing a protective barrier.

In the illustrative embodiment, the reduced-pressure, wound-closure and treatment system 100 is presented in the context of the abdominal cavity 110 and a surface wound 111, which has wound edges 112. Other subdermal tissue 114 may also have been opened, such as fat tissue, muscles, fascia, etc. The abdominal cavity 110 is shown with abdominal contents 116, which form a surface or support.

The reduced-pressure treatment subsystem 102 of the reduced-pressure, wound-closure and treatment system 100 helps to deliver reduced pressure to the tissue site 106 and the abdominal cavity 110. The reduced-pressure treatment subsystem 102 includes a manifold 118 disposed within the abdominal cavity 110 to distribute reduced pressure within the abdominal cavity 110 and to receive fluids. The manifold 118 may include or be associated with a manifold member 120, or second manifold, in a non-adherent envelope 122. The non-adherent envelope 122 has apertures 124 on a first side and apertures 126 on a second, inward-facing (tissue-facing) side. The apertures 124 and 126 facilitate flow of fluids as suggested by arrows 128. The apertures 124 and 126 may take any shape, such as rectangular openings, circular openings, polygons, slits (elongated slots), etc. The non-adherent envelope 122 may be formed from a flexible film, such as a polyurethane film, a drape material, or any non-adherent material.

Reduced pressure may be applied by reduced-pressure treatment subsystem 102 to the abdominal cavity 110 and the tissue site 106 to help promote removal of exudates, ascites, or other liquids, bacteria, fibrin, dead tissue, toxins, residual blood, etc. Reduced pressure may also be used in certain situations to stimulate growth of additional tissue. In the case of a wound at the tissue site 106, the growth of granulation tissue and removal of exudates and bacteria may help to promote healing of the wound. In the situation of a non-wounded or non-defective tissue, reduced pressure may be used to promote the growth of tissue that may be harvested and transplanted to another tissue site. In other situations, fluid removal may be the main reason for applying reduced pressure.

As used herein, "reduced pressure" generally refers to a pressure less than the ambient pressure at the tissue site 106. In most cases, the reduced pressure will be less than atmospheric pressure at which the patient is located. Alternatively, the reduced pressure may be less than the hydrostatic pressure of the tissue site 106. Unless otherwise indicated, values of pressure stated herein are gauge pressures.

The manifold 118 and manifold member 120 are disposed in the abdominal cavity 110 and may be disposed at or near the tissue site 106. Typically, the non-adherent envelope 122, which contains the manifold member 120, is disposed against the tissue site 106 and, in particular, proximate the abdominal contents 116. The manifold 118 is disposed adjacent the non-adherent envelope 122. The manifold 118 and manifold member 120 may take many forms. The term "manifold" as used herein generally refers to a substance or structure that is provided to assist in applying reduced pressure to, delivering fluids to, or removing fluids from a tissue site, such as tissue site 106. The manifold 118 and manifold member 120 typically include a plurality of flow channels or pathways that distribute fluids provided to and removed from the area proximate the manifold 118 and manifold member 120. In one embodiment, the manifold 118 and manifold member 120 include a plurality of flow channels or pathways that are interconnected to improve distribution of fluids. The manifold 118 and manifold member 120 may be formed from a biocompatible material that is capable of being placed in contact with tissue and that distributes reduced pressure. Examples of manifolds may include, without limitation, devices that have structural elements arranged to form flow channels, cellular foam, such as open-cell foam, porous tissue collections, and liquids, gels and foams that include or cure to include flow channels.

The manifold 118 and manifold member 120 may be porous and may be made from foam, gauze, felted mat, or any other material suited to a particular biological application. In one embodiment, the manifold 118 and manifold member 120 are made from a porous foam that includes a plurality of interconnected cells or pores that act as flow channels. The porous foam may be a polyurethane, open-cell, reticulated foam, such as a GranuFoam® material manufactured by Kinetic Concepts, Incorporated of San Antonio, Tex. Other embodiments may include "closed cells." In some situations, the manifold 118, the manifold member 120, and the non-adherent envelope 122 may be used to distribute fluids, such as medications, antibacterials, growth factors, and other solutions to the tissue site 106. Other layers may be included as part of the manifold 118 or manifold member 120, such as absorptive material, wicking material, hydrophobic material, and hydrophilic material.

A sealing member 132 may be placed over the surface wound 111 in epidermis 108 and, in particular, made to overlap the wound edges 112 to provide a pneumatic seal. Thus, the sealing member 132 provides a seal over the manifold 118 and the non-adherent envelope 122. The sealing member 132 may be a cover that is used to secure the manifold 118 and non-adherent envelope 122 at the tissue site 106. While the sealing member 132 may be impermeable or semi-permeable, the sealing member 132 is capable of maintaining a reduced pressure at the tissue site 106 after installation of the sealing member 132 over the manifold 118. The sealing member 132 may be a flexible over-drape or film formed from a silicone based compound, acrylic, hydrogel or hydrogel-forming material, or any other biocompatible material that includes the impermeability or permeability characteristics desired for the intended tissue site.

The sealing member 132 may further include an attachment device 136 to secure the sealing member 132 to a patient's epidermis 108. The attachment device 136 may take many forms; for example, a sealing tape might be used or an adhesive 134 may be positioned along a perimeter of the sealing member 132 or any portion of the sealing member 132 to provide a pneumatic seal. The adhesive 134 might also be pre-applied and covered with a releasable member (not shown) that is removed at the time of application.

A first reduced-pressure interface 138, such as a port 140 or connector, may be used to deliver reduced pressure from a first reduced-pressure delivery conduit 142 to the manifold 118. The first reduced-pressure interface 138 may also deliver any exudate, ascites, or other fluids from the manifold 118. The reduced pressure in the manifold 118 pulls the fluid in the direction shown by arrows 144 and to the first reduced-pressure delivery conduit 142. The first reduced-pressure interface 138 permits the passage of fluid from the manifold 118 to the first reduced-pressure delivery conduit 142. For example, fluids collected from the tissue site 106 using the manifold member 120 and the manifold 118 may enter the first reduced-pressure delivery conduit 142 via the first reduced-pressure interface 138. In another embodiment, the reduced-pressure treatment subsystem 102 may exclude the first reduced-pressure interface 138, and the first reduced-pressure delivery conduit 142 may be inserted directly into the sealing member 132 and the manifold 118. The first reduced-pressure delivery conduit 142 may be a medical conduit, multi-lumen member, tubing, or any other means for delivering a reduced pressure.

A reduced-pressure subsystem 148 may be used to supply the reduced pressure that is delivered to the first reduced-pressure delivery conduit 142. The reduced-pressure subsystem 148 may include a first reduced-pressure unit, or source, 150 that delivers reduced pressure to a conduit 152, which delivers the reduced pressure to a three-way valve 154. One portion of the reduced pressure may leave the three-way valve 154 through a second reduced-pressure delivery conduit 156. Another portion of the reduced pressure may leave the three-way valve 154 through a reduced-pressure conduit 158. Located on the reduced-pressure conduit 158 may be any number of devices, such as a reduced-pressure feedback unit 160, which may, for example, give feedback to the three-way valve 154 concerning the regulation of the reduced pressure within the reduced-pressure conduit 158. The reduced-pressure conduit 158 delivers the reduced pressure to a canister 162, which is operable to hold any fluids delivered to the canister 162 from the tissue site 106. Reduced pressure leaving the canister 162 is delivered to the first reduced-pressure delivery conduit 142. The first reduced-pressure delivery conduit 142 may be referred to as delivering a treatment-reduced-pressure because the reduced pressure therein has been placed, by the reduced-pressure subsystem 148, at the desired pressure and conditions for use in reduced-pressure treatment at the tissue site 106. The reduced pressure delivered to the first reduced-pressure delivery conduit 142 is typically selected to be in the range of −50 mm Hg to −500 mm Hg and more typically in the range of −100 mm Hg to −300 mm Hg at the tissue site 106.

A number of different devices, e.g., device 166, may be added to a medial portion 164 of the first reduced-pressure delivery conduit 142. The device 166 might be a pressure feedback device, a volume detection system, a blood detection system, an infection detection system, a flow monitoring system, a temperature monitoring system, etc. Some of these devices may be formed integrally to other parts; for example, the canister 162 may include one or more filters, e.g., a hydrophobic filter that prevents liquid from exiting.

There are many ways of developing or supplying the reduced pressure to be used with the reduced-pressure, wound-closure and treatment system 100. In the illustrative embodiment shown, the first reduced-pressure unit 150 is used for both applications, i.e., for wound closing and for reduced-pressure treatment. In an alternative embodiment, it may be desirable to use the first reduced-pressure unit 150 as the source for the second reduced-pressure delivery conduit 156 and have a second reduced-pressure unit 151 (shown in broken lines) to deliver reduced pressure to the reduced-pressure conduit 158.

As an aspect of the reduced-pressure, wound-closure and treatment system 100, it is also desirable to help provide a closing force to the surface wound 111 and in particular to apply a closing force between the wound edges 112. As shown in FIG. 1, the modular, reduced-pressure, wound-closure subsystem 104 may be used for this purpose. The modular, reduced-pressure, wound-closure subsystem 104 develops a closing force represented by arrows 170. The closing force is communicated to the epidermis 108 and urges the wound edges 112 towards each other. The modular, reduced-pressure, wound-closure subsystem 104 may be a stand-alone system for closing any surface wound or used as part of a larger system, e.g., the reduced-pressure, wound-closure and treatment system 100.

The modular, reduced-pressure, wound-closure subsystem 104 includes a spacing member, such as a flexible strap 171, which is shaped into a closed loop inboard of the wound edges 112 (see, e.g., FIG. 4), and a plurality of modular closing members 169 associated with the flexible strap 171. Alternatively, the spacing member may be one or more tie wires that hold the modular closing members 169 in a spaced relationship or a flexible adhesive film placed on top of the modular closing members 169 that hold the modular closing members 169 in a spaced relationship. Each modular closing member 169 has a sealed contracting member 195, a connection member 181, and an attachment member 211. Before forming the closed loop, the plurality of modular closing members 169, e.g., a first modular closing member 173 and a second modular closing member 175, are attached to the flexible strap 171. The plurality of modular closing members 169 is analogous to the modular closing members 308 in FIG. 2. The number of modular closing members 169 included on the flexible strap 171 is determined by the size of the loop needed to surround the surface wound 111.

Each modular closing member of the plurality of modular closing members 169 has a first end 177, which is typically placed inboard of the surface wound 111, and a second end 179, which is typically placed outboard of the surface wound 111. Each connection member 181 is coupled to the first end 177 of the corresponding modular closing member 169. In the illustrative embodiment of FIG. 1, each connection member 181 includes an attachment opening or loop 185 through which the flexible strap 171 may be placed. The attachment loops 185 allow each modular closing member 169 to be positioned in a desired location along the flexible strap 171.

A reduced-pressure interface 186 is coupled to each modular connection member 181. A plurality of reduced-pressure conduits 187 is fluidly coupled to the reduced-pressure interface 186 to provide reduced pressure thereto. The reduced pressure supplied through the second reduced-pressure delivery conduit 156 is fluidly coupled to a distributor 223 that is fluidly coupled to the plurality of reduced-pressure conduits 187 that are fluidly coupled to the plurality of reduced-pressure interfaces 186 to deliver reduced pressure to each modular closing member 169. For each modular closing member 169, the reduced-pressure interface 186 delivers reduced pressure to the sealed contracting member 195. Each reduced-pressure interface 186 may also function as a pin to hold the corresponding connection member 181 in place relative to the flexible strap 171.

Each modular closing member 169 of the modular, wound-closure subsystem 104 includes the sealed contracting member 195 that is used to develop a closing force. The sealed contracting member 195 may be formed from a contracting manifold material, which may be the same type of material as the manifold 118. Alternatively, it may be desirable to use a contracting manifold material that has fewer apertures or holes than the material used for the manifold 118. In addition, it may be desirable to have a material that will contract less in the vertical (for the orientation shown in FIG. 1) and more in the horizontal, or lateral, plane (for the orientation shown in FIG. 1). In an alternative embodiment, the sealed contracting member 195 may be formed with a pneumatic device to develop a closing force. For example, a chamber that collapses under reduced pressure may be used. The sealed contracting member 195 has a first side 190 and a second, inward-facing side 192. The sealed contracting member 195 is sealed to form a pneumatic seal about an interior space of the sealed contracting member 195.

Each connection member 181 of the plurality of modular closing members 169 includes a base 203 and a wall 209. The base 203 and wall 209 are formed integrally or are otherwise coupled by any technique, such as welding, bonding, adhesives, cements, etc. Each attachment member 211 has a base 213 and a wall 215. The base 213 and wall 215 of the attachment member 211 are formed integrally or otherwise coupled by any technique, such as those previously mentioned. An adhesive 197 or other attachment device may be used to hold the sealed contracting member 195 to the base 203 of the corresponding connection member 181. An adhesive 205 or other attachment device may be also be used to attach a peripheral edge 207 of the sealed contracting member 195 to a wall 209 of the corresponding connection member 181. An adhesive 217 or other attachment device may be used to hold the sealed contracting member 195 to the base 213 of the corresponding attachment member 211. An adhesive 219 or other attachment device may also be used to hold the sealed contracting member 195 to the wall 215 of the corresponding attachment member 211. An adhesive 227 or other attachment device may be used to releasably attach the base 213 to the epidermis 108 (or sealing member if already deployed on epidermis).

In operation, the reduced-pressure, wound-closure and treatment system 100 may be used in a body cavity, e.g., abdominal cavity 110, by first applying a manifold material on the abdominal contents 116. For example, the manifold member 120 with the non-adherent envelope 122 may be placed on the abdominal contents 116 and the manifold 118 disposed proximate the non-adherent envelope 122. The wound edges 112 of the surface wound 111 may be brought together to the extent possible, and then the sealing member 132 placed onto the epidermis 108 to provide a pneumatic seal over the surface wound 111.

The healthcare provider may measure or estimate the circumference of the surface wound 111 and then using a look-up table, determine the number of modular closing members 169, e.g., first modular closing member 173, which need to be added to the flexible strap 171. The flexible strap 171 is also cut or otherwise sized to a proper length. The plurality of modular closing members 169, e.g., modular closing members 173 and 175, desired are added to the flexible strap 171. The flexible strap 171 is formed into a closed loop that has a circumference less than the circumference of the surface wound 111. The closed loop is substantially centered on the surface wound 111 and each of the attachment members 211 are secured to the patient's epidermis 108 (or to the sealing member 132). In this regard, as used herein, references to attaching to the patient's epidermis 108 should be deemed to include attachment to a sealing member 132 on the epidermis 108.

The first reduced-pressure interface 138, which may be the reduced-pressure port 140, may be applied such that an extended portion 202 reaches into the manifold 118. The first reduced-pressure delivery conduit 142 may be coupled to the first reduced-pressure interface 138 to provide a fluid coupling with the first reduced-pressure unit 150 (or an optional second reduced-pressure unit 151). The second reduced-pressure delivery conduit 156 may be fluidly coupled to the distributor 223. The plurality of reduced-pressure conduits 187 are fluidly coupled to the distributor 223 and to the plurality of reduced-pressure interfaces 186.

The reduced-pressure, wound-closure and treatment system 100 is activated such that the first reduced-pressure unit 150 delivers reduced pressure through the three-way valve 154, which prepares the treatment-reduced-pressure that is delivered to the first reduced-pressure delivery conduit 142 and a closing-reduced-pressure that is delivered to the second reduced-pressure delivery conduit 156. The treatment-reduced-pressure delivered through the first reduced-pressure delivery conduit 142 is realized at the manifold 118, which pulls fluids as suggested by arrows 144 and 128 and distributes reduced pressure within the abdominal cavity 110. The closing-reduced-pressure is delivered through the second reduced-pressure delivery conduit 156 to the distributor 223 and through the plurality of reduced-pressure conduits 187 to the plurality of modular closing members 169. The closing-reduced-pressure is received by the plurality of modular closing members 169 and is delivered to the interior of each of the sealed contracting member 195, and causes each of the sealed contracting members 195 to contract and thereby to develop a closing force between the flexible strap 171 and the attachment members 211. The net result is to provide a closing force urging the wound edges 112 inward.

Figure 2:
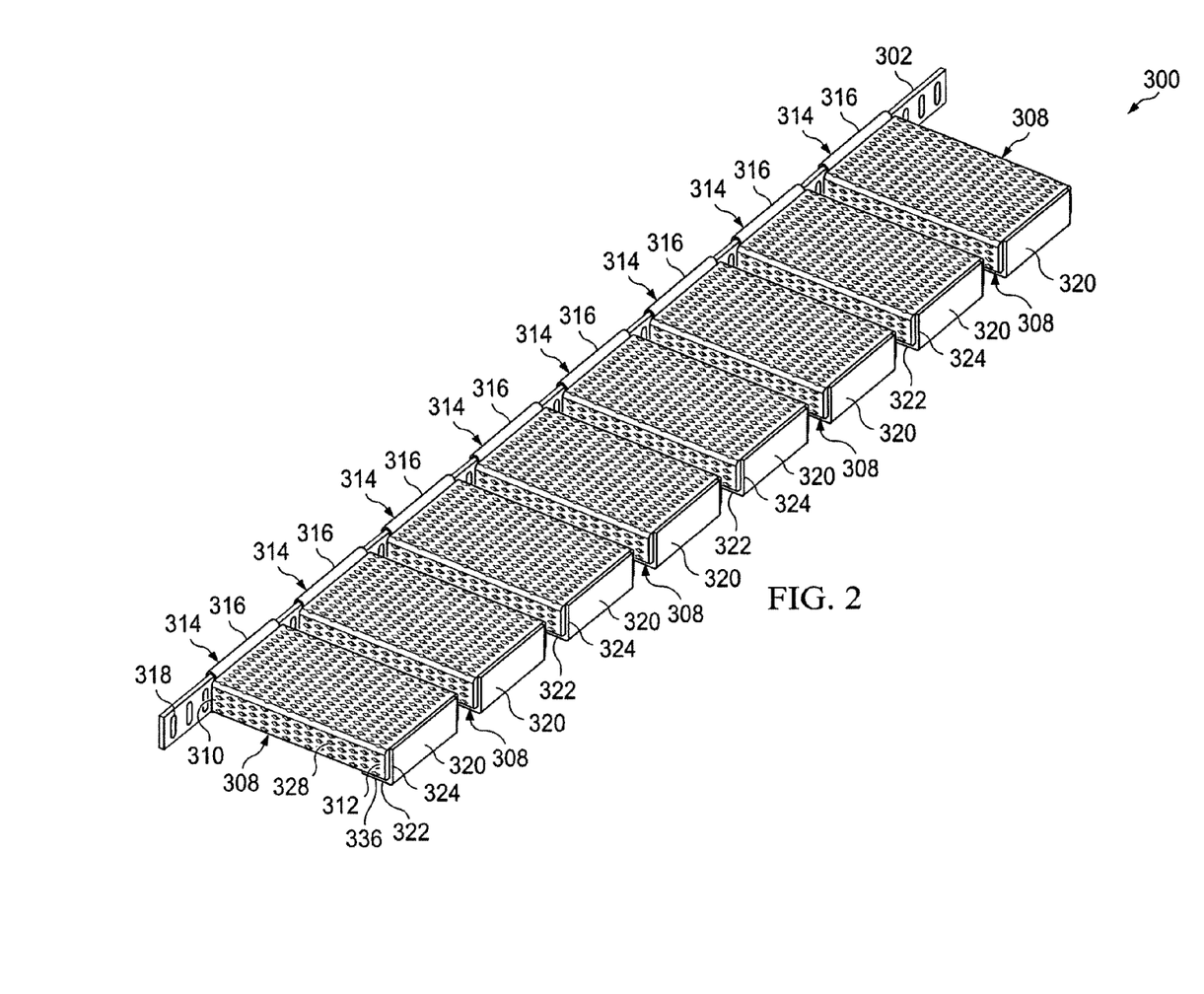
FIG. 2 is a schematic, perspective view of an illustrative embodiment of a portion of a modular, reduced-pressure, wound-closure system.
Figure 3:
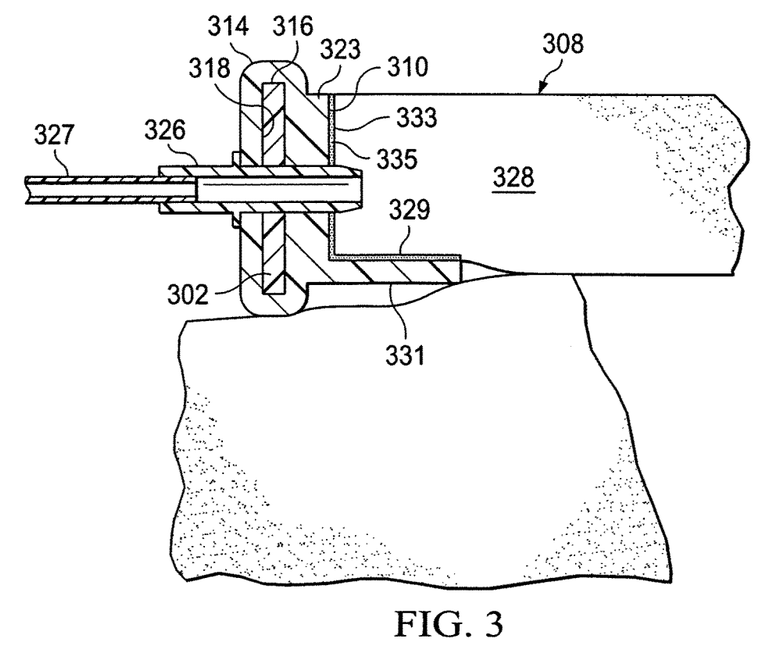
FIG. 3 is a schematic, cross-section of a portion of a modular closing member of the modular, reduced-pressure, wound-closure system of FIG. 2.
Figure 4:
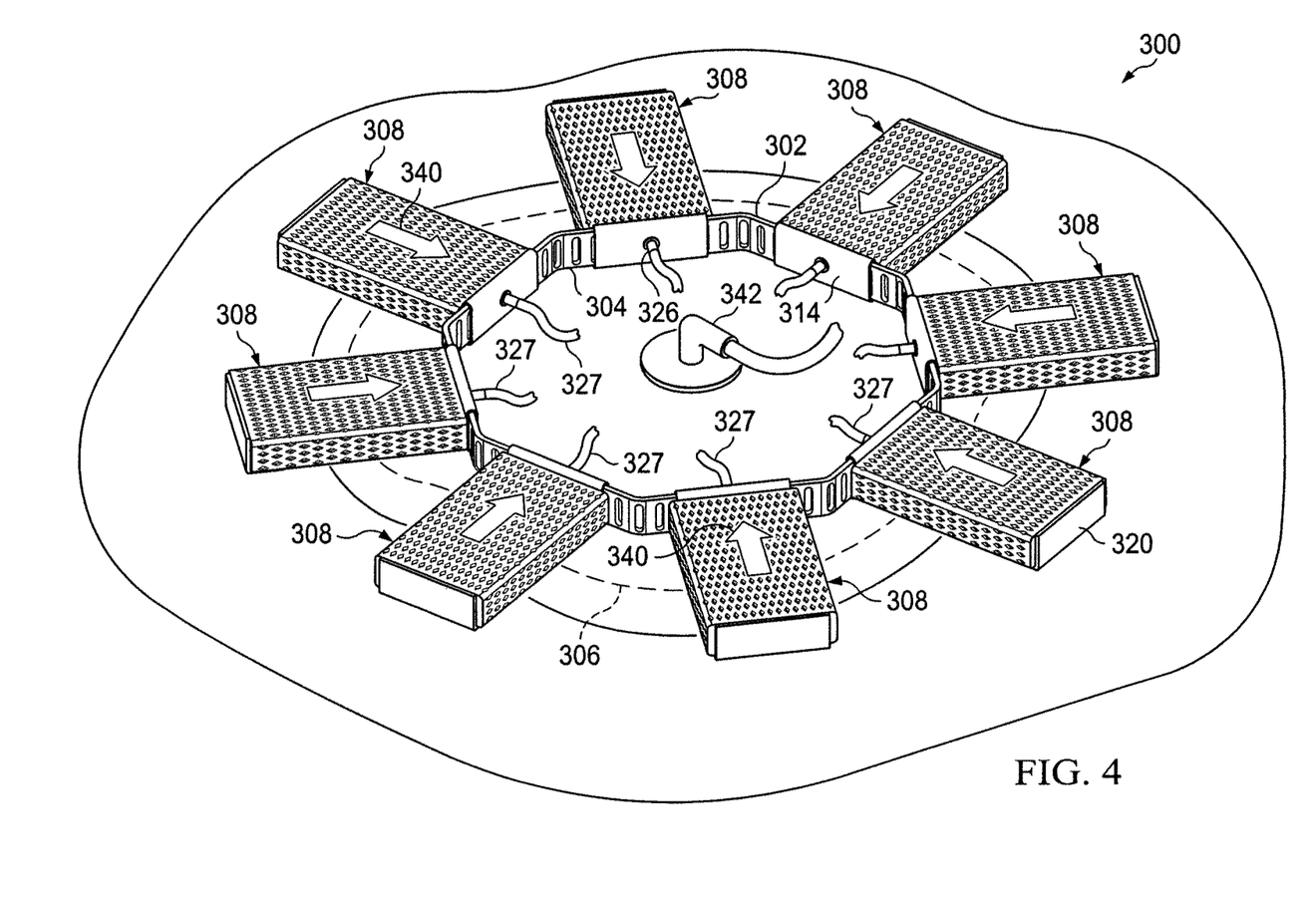
FIG. 4 is a schematic, perspective view of the illustrative modular, reduced-pressure, wound-closure system of FIGS. 2-3 shown deployed over a surface wound of a patient.

Referring now to FIGS. 2-4, an illustrative embodiment of a modular, reduced-pressure, wound-closure system 300 is presented. The modular, reduced-pressure, wound-closure system 300 may be used as the modular, wound-closure subsystem 104 of FIG. 1. The modular, reduced-pressure, wound-closure system 300 may include a flexible strap 302 with a plurality of modular closing members 308. Each modular closing member 308 includes an attachment member 320 and a connection member 314. Use of modular members 308 allows numerous sizes and shapes of surface wounds to be accommodated without requiring a large stock of different sizes and shapes of wound dressings or devices.

The flexible strap 302 is shown in a linear position in FIG. 2 and shaped into a closed loop 304 in FIG. 4. The flexible strap 302 is shaped into the closed loop 304 around a surface wound 306, such as an opening on a patient's epidermis. The plurality of modular closing members 308 is selectively coupled to the flexible strap 302. The number of modular closing members 308 included on the flexible strap 302 is determined by the size of the closed loop 304 needed to surround the surface wound 306. Thus, to surround the surface wound 306 in FIG. 4, eight modular closing members 308 have been included on the flexible strap 302. Referring again to FIG. 2, each modular closing member 308 has a first end 310 and a second end 312.

Each connection member 314 is coupled to the first end 310 of each modular closing member 308. In the illustrative embodiment of FIG. 2, each connection member 314 includes an attachment loop or opening 316 through which the flexible strap 302 may be placed. The attachment loops 316 allow each modular closing member 308 to be positioned in a desired location along the flexible strap 302. A portion of each attachment loop 316 may interface with a strap opening 318 to help hold the connection member 314 in position on the flexible strap 302. Alternatively or in addition, a reduced-pressure interface 326 may function as a peg to hold the connection member 314 in place relative to the flexible strap 302.

Referring now primarily to FIG. 3, a connection member 314 is presented. The reduced-pressure interface 326 is shown coupled to the connection member 314. A reduced-pressure conduit 327 is fluidly coupled to the reduced-pressure interface 326 to provide reduced pressure to the reduced-pressure interface 326. The reduced-pressure interface 326 delivers the reduced pressure to a sealed contracting member 328 and, as previously mentioned, the reduced-pressure interface 326 may function as a pin to hold the connection member 314 in place relative to the flexible strap 302.

The sealed contracting member 328 is made of the same or similar materials as the previously mentioned sealed contracting member 195 of FIG. 1. The sealed contracting member 328 is sealed to form a pneumatic seal about an interior space of the sealed contracting member 328. An adhesive 329 or other attachment device (e.g., cement, weld, hooks, etc.) may be used to hold the sealed contracting member 328 to a base 331. An adhesive 335 or other attachment device (e.g., cement, weld, hooks, etc.) may be also be used to attach a peripheral edge 333 of the sealed contracting member 328 to a wall 323 of the connection member 314.

Referring again primarily to FIG. 2, an attachment member 320 may be coupled to each of the second ends 312 of the sealed contracting member 328. Each of the attachment members 320 may be formed with a base 322 and a wall 324. An adhesive (not explicitly shown) or other attachment device (e.g., cement, weld, hooks, etc.) may be used to hold the sealed contracting member 328 to the base 322. An adhesive (not explicitly shown) or other attachment device (e.g., cement, weld, hooks, etc.) may also be used to hold the sealed contracting member 328 to the wall 324.

Figure 5:
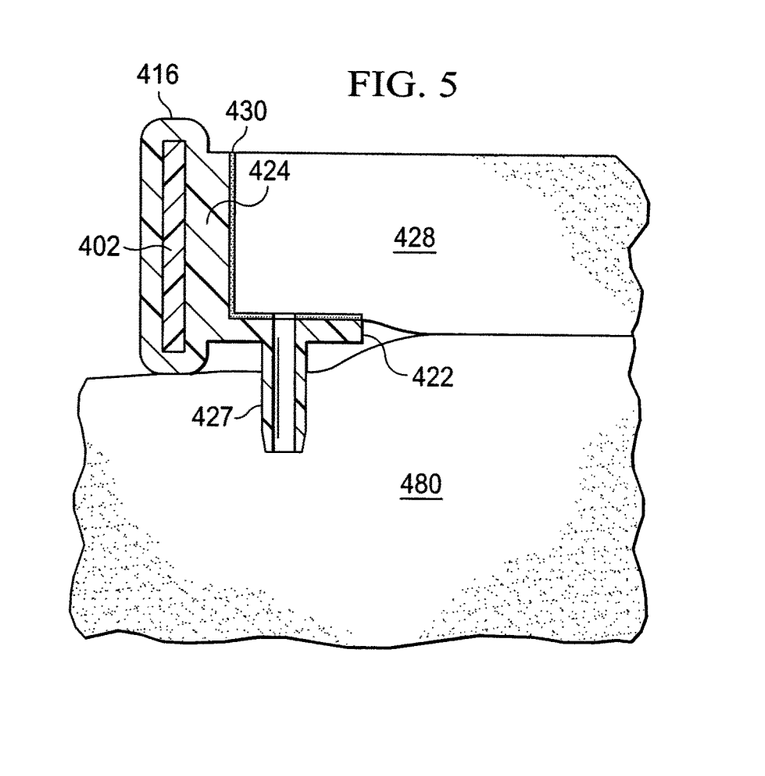
FIG. 5 is a schematic, cross-sectional view of an illustrative embodiment of a portion of a modular closing member.

Referring now primarily to FIG. 5, an alternative reduced-pressure interface 427 is presented as part of a connection member 416. Reduced pressure may be provided to a sealed contracting member 428 through the connection member 416. The connection member 416 selectively attaches to a flexible strap 402. An adhesive 430 may be used to hold the sealed contracting member 428 to the connection member 416. The connection member 416 may have a wall 424 and a base 422 that are formed integrally or otherwise coupled by any technique, e.g., welding (RF weld or ultrasonic), bonding, adhesives, cements, etc. The reduced-pressure interface 427 may be formed on the base 422 and configured to enter a manifold 480, or manifold pad. The reduced-pressure interface 427 is sized and configured to engage the manifold 480, which is in fluid communication with, or is fluidly coupled to, a reduced pressure source. The reduced pressure is delivered to the manifold 480 which communicates the reduced pressure through the reduced-pressure interface 427 to the sealed contracting member 428.

Referring again primarily to FIGS. 2-4, one illustrative method of operating the modular, reduced-pressure, wound-closure system 300 will be presented. In operation, a healthcare provider assesses the size of the surface wound 306 and determines the number of modular closing members 308 that are appropriate for the size of the surface wound 306. A look-up chart or table based on a measurement of the circumference of the surface wound 306 may be used to suggest the appropriate number of the modular closing members 308. The appropriate number of the modular closing members 308 is then selectively coupled to the flexible strap 302. The flexible strap 302 is then shaped into the closed loop 304, which is preferably sized to be inboard of the peripheral edges of surface wound 306. The flexible strap 302 is secured to form the closed loop 304 using any number of means, such as a ratchet, snap, fastener, ratchet ties, flexible peg and slot members, etc. Then, each of the plurality of attachment members 320 is attached to the patient's epidermis proximate the edge of the surface wound 306. As before, the statement that the attachment members 320 are attached to the epidermis may include that the attachment members 320 are attached to a sealing member being used for reduced-pressure treatment.

In applying each attachment member 320, the base 322 may have an adhesive (see adhesive 227 in FIG. 1) or other attachment device applied on a second, inward-facing surface 336. The adhesive may have a releasable backing on the adhesive that is removed prior to use. Thus, the healthcare provider would pull off the backing, exposing the adhesive, and then press the adhesive on the epidermis (or sealing member). Then, each reduced-pressure interface 326 associated with each of the plurality of connection members 314 is coupled to a reduced-pressure source, such as by a reduced-pressure conduit 327 or a distributor (not shown). (Alternatively, the reduced-pressure interface 427 of FIG. 5 may have already been introduced into the manifold 480 if used.) After activating the reduced-pressure source, reduced pressure is supplied to the reduced-pressure conduit 327 which delivers the reduced pressure through the reduced-pressure interface 326 to the sealed contracting member 328. The reduced pressure causes the sealed contracting member 328 to contract. As the sealed contracting member 328 contracts, the sealed contracting member 328 develops a closing force represented by arrows 340 in FIG. 4. The closed loop 304 remains substantially in relative position, and thus each attachment member 320 pulls the epidermis inward.

The closed loop 304 provides an open area in the middle of the closed loop 304 that readily accommodates a reduced-pressure interface 342 if reduced-pressure treatment is also desired. The reduced-pressure interface 342 may be used to supply reduced pressure to a reduced-pressure treatment system (see, e.g., reduced-pressure treatment subsystem 102 in FIG. 1).

Figure 6:
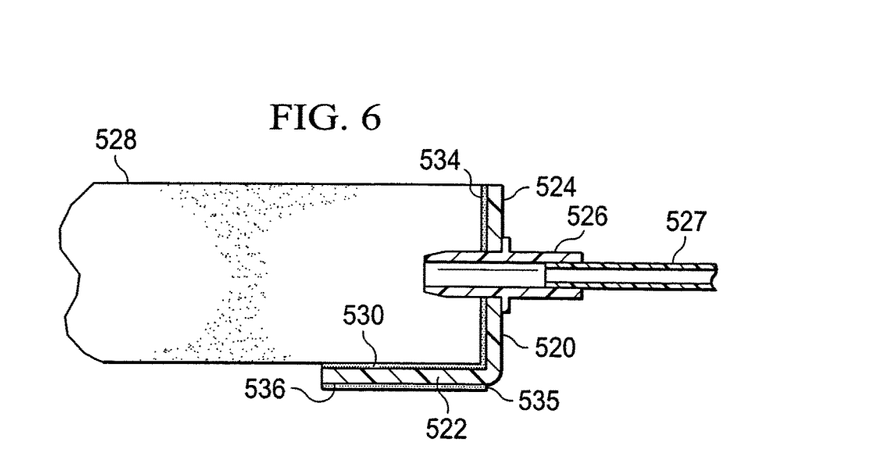
FIG. 6 is a schematic, cross-sectional view of an illustrative embodiment of a portion of a modular closing member.

Referring now primarily to FIG. 6, another alternative, illustrative embodiment of a reduced-pressure interface 526 is presented. The reduced-pressure interface 526 is formed as part of an attachment member 520. The attachment member 520 includes a base 522 and a wall 524 formed integrally or otherwise coupled. An adhesive 530 or other attachment device (e.g., bond, cements, weld, etc.) may hold, or secure, a portion of a contracting member 528 to the base 522. An adhesive 534 or other attachment device (e.g., bond, cements, weld, etc.) may hold a portion of the contracting member 528 to the wall 524. An adhesive 535 or other attachment device (e.g., bond, cements, suture, etc.) on a inward-facing side 536 of the base 522 may be used to attach the base 522 to a patient's epidermis (or sealing member). In this illustrative embodiment, the reduced-pressure interface 526, which is fluidly coupled to a reduced-pressure conduit 527, extends through the wall 524 and delivers reduced pressure to the sealed contracting member 528.

Referring again to FIG. 4, another embodiment will be presented. In this alternative embodiment, a set number of the modular closing members 308 are slideably attached to the strap 302 and may be provided in a closure kit as such. When applying the wound-closure system 300, the healthcare provider appropriately spaces the set number of modular closing members 308—usually equidistant from one another—on a portion of the strap 302 to be used and forms the closed loop 304. Any extra portion of the strap 302, i.e., a portion not needed to form the closed loop 304, may be cut and removed.

According to another illustrative embodiment, a modular wound closure system for closing a wound on a patient's epidermis using reduced pressure includes a plurality of closing devices that contract when under the influence of reduced pressure. Each of the closing devices have a distal end and a proximal end. The system further includes a flexible member for maintaining the plurality of closing devices in a spaced relationship with the proximal ends inboard of an edge of the wound. The system also includes a plurality of attachment apparatuses for releaseably coupling the distal ends of the plurality of closing devices to the patient's epidermis outboard of the edge of the wound. The system further includes a plurality of reduced-pressure connectors for providing reduced pressure to the plurality of closing devices. The plurality of closing devices may be formed as a plurality of sealed contracting members. The plurality of closing devices may be detachably mated to the flexible member. The plurality of closing devices have a first volume (V1) at an ambient pressure and have a second volume (V2) at a reduced pressure and wherein V1>V2. The plurality of closing devices may be slideably mated to the flexible member.

Although the present invention and its advantages have been disclosed in the context of certain illustrative, non-limiting embodiments, it should be understood that various changes, substitutions, permutations, and alterations can be made without departing from the scope of the invention as defined by the appended claims.

We claim:

1. A method of treating a wound, the method comprising:
   placing a loop of closing members on a surface proximate to the wound, wherein the loop is placed within a perimeter of the wound, and wherein the closing members are spaced around the wound on the surface;
   securing an end of each closing member to the surface; and
   contracting the closing members with reduced pressure applied to contracting members sealed within each closing member such that each closing member provides a closing force on the wound.

2. The method of claim 1, wherein the surface is an epidermis.

3. The method of claim 1, wherein the surface is a sealing member applied to an epidermis proximate to the wound.

4. The method of claim 1, wherein placing the loop of closing members on the surface comprises sizing the loop based on a circumference of the wound.

5. The method of claim 1, wherein placing the loop of closing members on the surface comprises:
   determining a number of closing members to be placed based on a size of the wound; and
   sizing the loop based on the number of closing members.

6. The method of claim 1, wherein placing the loop of closing members on the surface comprises:
   determining a number of closing members to be placed based on a size of the wound;
   coupling the determined number of the closing members to a spacing member;
   sizing the spacing member; and
   forming the loop from the spacing member with the determined number of the closing members.

7. The method of claim 1, wherein each of the contracting members comprises a porous foam.

8. A method of treating a tissue site, the method comprising:
   placing a non-adherent envelope containing a manifold member on abdominal contents;

sealing a wound in the epidermis with a sealing member;
placing a loop of closing members on a surface proximate to the wound in the epidermis, wherein the loop is placed within a perimeter of the wound, and wherein the closing members are spaced around the wound on the surface;
attaching an end of each closing member to the surface;
distributing reduced pressure to an abdominal cavity through the manifold member on the abdominal cavity;
contracting the closing members with a reduced pressure applied to contracting members sealed within each closing member such that each closing member provides a closing force on the wound.

9. The method of claim 8, further comprising:
placing a second manifold member adjacent to the non-adherent envelope in the abdominal cavity; and
distributing the reduced pressure through the second manifold member.

10. The method of claim 8, further comprising:
placing a second manifold member adjacent to the non-adherent envelope and proximate to subdermal tissue in the abdominal cavity; and
distributing the reduced pressure through the second manifold member.

11. The method of claim 8, wherein the surface is the epidermis.

12. The method of claim 8, wherein the surface is the sealing member.

\* \* \* \* \*